US00RE34564E

United States Patent [19]

Mar et al.

[11] E Patent Number: Re. 34,564

[45] Reissued Date of Patent: Mar. 15, 1994

[54] LIQUID FILLED LOW PROFILE DILATATION CATHETER

[75] Inventors: Craig E. Mar, Fremont; Jeffrey S. Frisbie, San Jose, both of Calif.

[73] Assignee: Advanced Cardiovascular Systems, Inc., Santa Clara, Calif.

[21] Appl. No.: 634,670

[22] Filed: Dec. 27, 1990

Related U.S. Patent Documents

Reissue of:

[64] Patent No.: 4,793,350
Issued: Dec. 27, 1988
Appl. No.: 648
Filed: Jan. 6, 1987

[51] Int. Cl.[5] ..... A61M 29/02

[52] U.S. Cl. ..... 604/96; 606/194

[58] Field of Search ..... 604/96-101; 128/207.15; 606/191-195

[56] References Cited

U.S. PATENT DOCUMENTS

| | | | |
|---|---|---|---|
| 4,261,339 | 4/1981 | Hanson et al. | 128/344 |
| 4,483,340 | 11/1984 | Fogarty et al. | 128/344 |
| 4,538,622 | 9/1985 | Samson et al. | 604/170 |
| 4,619,263 | 10/1986 | Frisbie et al. | 128/344 |
| 4,638,805 | 1/1987 | Powell | 128/344 |
| 4,715,378 | 12/1987 | Pope, Jr. et al. | 604/96 |
| 4,723,936 | 2/1988 | Bachbinder et al. | 604/96 |
| 4,762,129 | 8/1988 | Bonzel | 604/96 |

FOREIGN PATENT DOCUMENTS

| | | | |
|---|---|---|---|
| 0213748 | 3/1987 | European Pat. Off. | 128/344 |

*Primary Examiner*—Stephen C. Pellegrino
*Assistant Examiner*—William Lewis
*Attorney, Agent, or Firm*—Crosby, Heafey, Roach & May

[57] ABSTRACT

Low profile dilatation catheter having an elongate flexible tubular member with proximal and distal extremities and with a flow passage extending therethrough. An inflatable balloon is mounted on the distal extremity of the elongate flexible tubular member so that the balloon has its interior in communication with the flow passage in the tubular member. A flexible tip is secured to the distal extremity of the balloon. A core wire extends through the elongate flexible member and has proximal and distal extremities. The distal extremity of the core wire is tapered and extends through the balloon and into the flexible tip. The distal extremity of the core wire is secured to the flexible tip. A rotator is provided for rotating the proximal extremity of the core wire for causing rotation of the flexible tip. Self-venting means is provided for venting the balloon to ambient. An adapter is carried by the proximal extremity of the elongate tubular member. A liquid is supplied to the adapter and the flow passage for inflating and deflating the inflatable balloon.

14 Claims, 1 Drawing Sheet

LIQUID FILLED LOW PROFILE DILATATION CATHETER

Matter enclosed in heavy brackets [ ] appears in the original patent but forms no part of this reissue specification; matter printed in italics indicates the additions made by reissue.

This invention relates to a low profile dilatation catheter and more particularly, to a liquid filled dilatation catheter.

In co-pending application Ser. No. 760,635, filed July 30, 1985, now U.S. Pat. No. 4,664,113, there is disclosed a gas filled low profile dilatation catheter movable within another larger profile dilatation catheter the low profile dilatation catheter is capable of passing through a lumen having a diameter of approximately 0.020 inches. Because of the concern of introducing into a gas filled catheter in the patients's vessel, there is a need for a low profile dilatation catheter which eliminates the use of gas.

In general, it is an object of the present invention to provide a low profile dilatation catheter which is liquid filled.

Another object of the invention is to provide a dilatation catheter of the above character which is relatively rigid so that it can be advanced in a guiding catheter.

Another object of the invention is to provide a dilatation catheter of the above character in which liquid can pass relatively easily throughout the entire length of the dilatation catheter to make possible inflation and deflation of the balloon in relatively short periods of time.

Additional objects and features of the invention will appear from the following description in which the preferred embodiment is set forth in detail in conjunction with the accompanying drawing.

Figure 1:
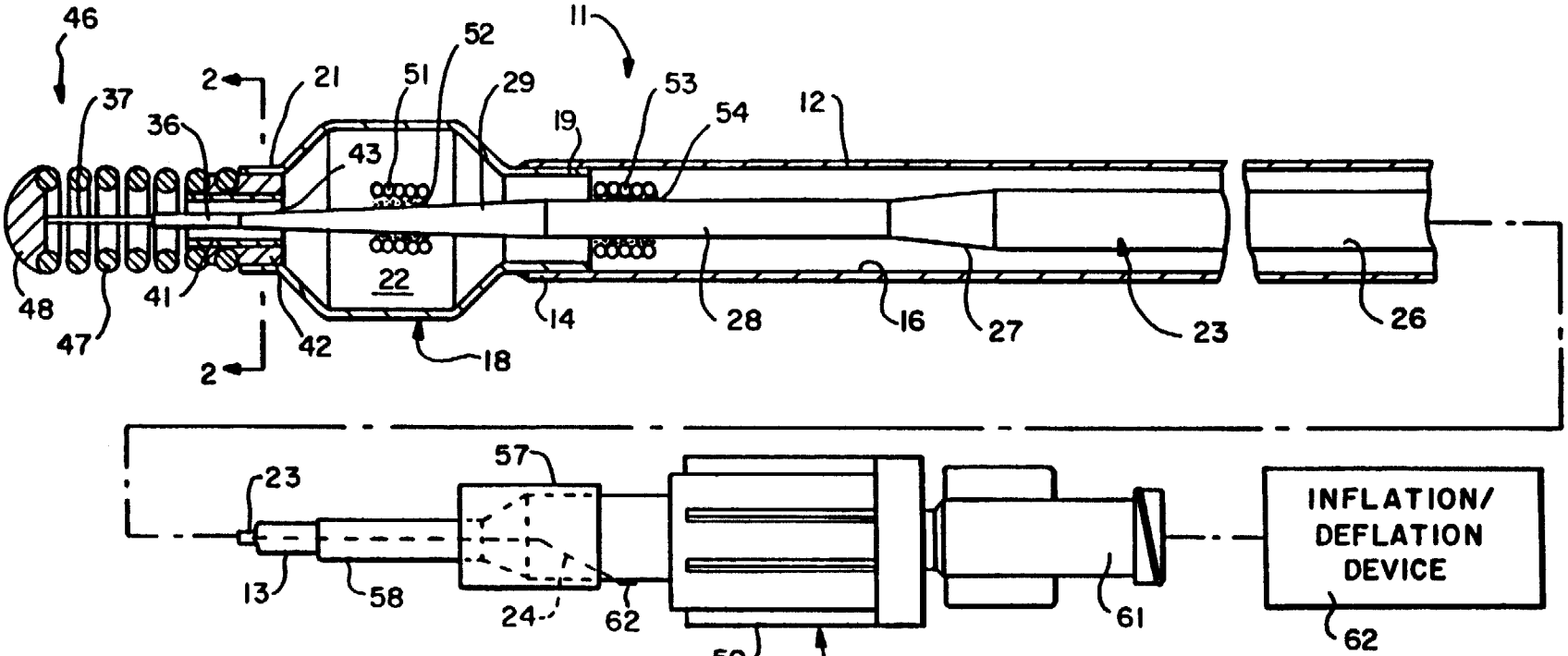
FIG. 1 is a cross-sectional view of a liquid filled low profile dilatation catheter incorporating the present invention.

In general the liquid filled low profile dilatation catheter of the present invention consists of an elongate flexible tubular member having proximal and distal ends and having a flow passage extending therethrough. An inflatable balloon is mounted on the distal end of the flexible tubular member and has its interior in communication with the flow passage. A coil spring is secured to the distal extremity of the balloon. A guide wire is provided which extends through the elongate flexible tubular member and has proximal and distal extremities. The distal extremity of the guide wire is tapered and extends through the balloon and through the coil spring. Means is provided which secures the distal extremity of the guide wire to the distal extremity of the spring. Self-venting means is provided for venting air from the balloon. An adapter is carried by the proximal extremity of the flexible elongate tubular member to permit liquid to be introduced into the flow passage for inflating and deflating the balloon. Means is provided permitting rotation of the guide wire so that the extremity of the coil tip can be rotated.

More in particular as shown in the drawing, the liquid filled low profile balloon dilatation catheter 11 consists of a flexible elongate tubular member 12 having proximal and distal ends 13 and 14 and having a flow passage or lumen 16 extending therethrough. Because it is desired to provide a catheter which has a very low profile, it is important the tubular member 12 be formed of a material which has a very small wall thickness and which still has sufficient rigidity so that the catheter can be advanced in through a guiding catheter into a patient's vessel. One material found to be particularly satisfactory for this purpose is polyimide tubing which has a wall thickness of 0.001 inches. With such a wall thickness, it is possible to provide a tubular member 12 which has an inside diameter of 0.016 inches and an outside diameter of 0.018 inches and still provide a tubular member which has an outer diameter which is less that 0.020 inches which is the inner diameter through which the dilation catheter 11 must pass. The tubular member 12 has a suitable length such as approximately 175 centimeters.

A separate balloon member 18 has been provided having proximal and distal ends 19 and 21. The balloon member 18 can be formed of a suitable material such as an irradiated polyethylene which is blown into the desired configuration as shown and having an inflated size which is less than approximately 2.0 millimeters and preferably a size of approximately 1.5 millimeters. The balloon member 18 should have a wall thickness of sufficient strength so that it can stand suitable pressures, as for example 10 to 15 atmospheres, or in other words, approximately 200 psi. As can be seen, the proximal and distal extremities 19 and 21 of the balloon member are necked down to the desired diameters. For examples, the proximal extremity 19 has been necked down so it has a size so that it can fit within the distal extremity 14 of the tubular member 12. The proximal extremity 19 is secured in the distal extremity 14 by suitable means such as an adhesive. The interior 22 of the balloon member 18 is in communication with the flow passage 16.

A guide wire 23 formed of a suitable material such as stainless steel forms a part of the catheter 11 and extends through the flow passage 16 and through the interior of the balloon member 18 and beyond the distal extremity of the balloon member 18. The guide wire 23 is provided with multiple tapers. In order to provide suitable space for the passage of liquid through the tubular member 12 in the flow passage 16, the guide wire 23 has a limited diameter as, for example, less than approximately 0.012 inches and preferably a diameter of 0.010 inches extending from its proximal extremity 24. Thus, the proximal portion 26 of the guide wire 23 has a constant diameter of 0.010 inches for a length of 140 centimeters assuming that the dilatation catheter 11 has a length of approximately 175 centimeters. A tapered portion 27 having a length of approximately 3 centimeters is then provided which steps the diameter down from 0.010 inch to 0.006 inch. This is followed by a portion 28 of constant diameter of a length of 35 centimeters. An additional tapered portion 29 of a length of 3 centimeters is provided, which is within the interior of the balloon member 18. This tapered portion 29 step the diameter of the guide wire down to 0.003 inch to a portion 36 of constant diameter having a diameter of 0.003 inch and having a length of approximately 1 centimeters. The distal extremity 37 of the guide wire 23 is flattened so that it has a thickness of approximately 0.0012 inch and a width of approximately of 0.005 inch and a length of approximately 1 centimeters.

A small capillary tube 41 is disposed within the distal extremity 21 of the balloon member 18 and is secured therein by suitable means such as adhesive 42. The capillary tube 41 has an interior diameter of approximately 0.0031 inch so that there is provided a self-venting passage 43 between the core guide wire 23 and the inside diameter of the capillary tube 41 having a radial dimension of approximately 0.001505 inch for venting any air in the interior of the balloon member 18 to ambient through a flexible coil spring tip 46 when the balloon member 18 is filled with a liquid as hereinafter described.

The tip 46 is formed of a suitable radiopaque material such as platinum. For example, platinum wire having a diameter of 0.003 inch wound on a mandrel of 0.008 inch can be utilized to provide a coil 47 which has an outside diameter of 0.016 inch. The proximal extremity of the coil 47 extends over the capillary tube 41 and is secured adjacent to the distal extremity of the balloon member 18 by the adhesive 42. Means is provided for securing the distal extremity of the coil 47 to the distal extremity 37 of the guide wire 23 and consists of a solder joint 48 formed of a suitable material such as gold which has its exterior surface bonded in the form of a semi-hemisphere.

Suitable means is provided for marking the location of the balloon member 18 and consists of a marker 51 disposed on the interior of the balloon and carried by the core wire 23. By way of example, the marker 51 can be formed of platinum wire having a diameter of 0.002 inches wound onto the core wire 23 and secured intermediate the ends of the balloon member 18 as shown particularly in FIG. 1 by suitable means such as an adhesive 52. In addition or alternatively, an additional marker 53 formed of platinum wire having a diameter of 0.003 inch can be secured to the portion 28 of the core wire 23 just proximal of the proximal extremity of the balloon 18 by suitable means such as an adhesive 54.

An adapter 56 is provided on the proximal extremity 13 of the tubular member 12. The adapter 56 takes the form of a threaded fitting 57 which receives the proximal extremity of the tubular member 12 through a threaded reinforcing sleeve 58. The fitting 57 is mounted on a rotating hemostatic rotater 59 of a conventional construction which carries a winged Luer-type fitting 61. The Luer-type fitting 61 is adapted to be coupled to a device for injecting liquid into the flow passage 16 of the tubular member 12, for example, a device 62 such as disclosed in U.S. Pat. No. 4,439,185.

Means is provided for securing the proximal extremity 24 of the core wire 23 to permit rotation of the core wire 23 so as to make possible manipulation of the distal extremity of the tip 46. In the present embodiment this has been accomplished by bringing the proximal extremity 24 of the core wire 23 out through the threaded fitting 57 and securing the same to the rotater 59 by suitable means such as an adhesive at the region 62.

Operation and use of the balloon dilatation catheter 11 may now be briefly described as follows. The balloon member 18 can be inflated and deflated by attaching the inflation device to the Luer-type fitting 61 and filling the balloon with a suitable liquid such as radiopaque contrast liquid and observing the balloon to force all of the air out of the balloon through the vent 43. After it has been observed that all the air has been removed from the balloon 18, the balloon can be deflated so that it has a minimum diameter.

The dilatation catheter 11 can then be inserted into a guiding catheter (not shown) already positioned in the vessel of the patient in a conventional manner. If it is to be used with a dilatation catheter having a larger balloon size, the dilation catheter having the larger balloon is first inserted after which the dilatation catheter of the present invention can be inserted in the other dilatation catheter. The smaller dilatation catheter of the present invention can then be advanced into proximity of the stenosis. The spring tip 46, before introduction into the patient, can be provided with a desired bend in the flattened portion 37 of the core wire 23 as well as the coil 47 of the tip 46. After it is located adjacent to the stenosis, the tip can be rotated through approximately 360° with ease by rotating the rotator 59. It has been found that since the proximal extremity 24 of the core wire 23 is secured to the rotator 59 that the core wire 23 in conjunction with the stiffness provided by the tubular member 12 makes it possible to obtain a full 360° rotation of the flexible tip 46 with approximately the same amount of rotation on the proximal extremity of the catheter 11 or, in other words, one-for-one tracking. This provides excellent directional control of the flexible tip 46 and facilitate insertion of the flexible tip 46 into the opening in a stenosis. This rotation of the tip is facilitated by the presence of the capillary tube 41 through which the core wire 23 extends. The annular vent ensures that minimal friction is placed on the core wire 23 as it is rotated. *The rotation of the core wire 23 contracts or expands the expanded turns of the coil 47 depending upon the direction of rotation so that the distal end of the balloon member 18 secured to the proximal end of the coil does not rotate and cause the balloon member to wrap upon the rotation of the core wire.*

After the spring wire tip 46 has entered the stenosis, the deflated balloon can be positioned in the stenosis while observing the marker 51. After the balloon member 18 is in the desired position, it can be inflated to enlarge the opening in the stenosis. Thereafter the balloon member can be deflated and withdrawn from the stenosis and if desired, a larger balloon carried by the other dilatation catheter can then be advanced into the opening provided by the balloon member 18 and the opening still further enlarged by inflating the balloon of the other catheter having the desired size. After the balloon is then deflated, both of the balloon dilatation catheters can be removed.

Figure 3:
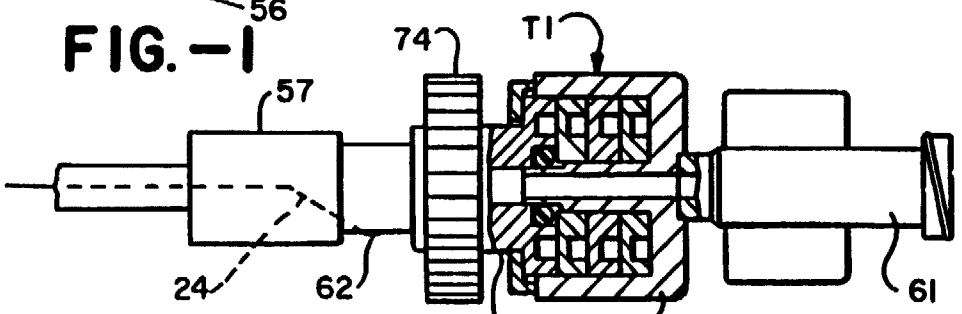
FIG. 3 is a partial cross-sectional view of the proximal extremity of another embodiment of a catheter incorporating the present invention.
Figure 2:
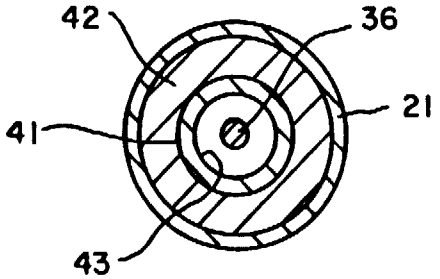
FIG. 2 is a cross-sectional view taken along the line 2—2 of FIG. 1.

Another embodiment of a balloon dilatation catheter incorporating the present invention is shown in Figure 3 in which a rotation limiting device 71 is provided between the rotator 59 and the winged fitting 61. The device 71 can be of the type disclosed in Ser. No. 760,635 filed July 30, 1985 in which the outer housing 72 is secured to the winged fitting 61 and the inner hub 73 is secured to the fitting 57. A knurled knob 74 is provided on the hub 73 for rotating the fitting 57 within the limits permitted by the device 71, as for example, up to three turns. This prevents undue twisting of the balloon member 18. From the foregoing, it can be seen that there has been provided a balloon dilatation catheter which has a very small profile and which still can be liquid filled, thus eliminating the danger of introducing any gas into the blood vessel of a patient. By providing the tubular member 12 having a very thin wall, it is still possible to provide good torquing characteristics with the guide wire and still provide an adequate flow passage for the flow of liquid into and out of the balloon to make possible the inflation and deflation of the balloon in relatively short periods of time. In addition, the catheter still has excellent torquing characteristics making possible a 360° rotation of the flexible tip. Rotation of the tip is made relatively easy because of the presence of the capillary tube through which the core wire extends. Rotation limiting is provided to prevent twisting of the balloon.

What is claimed is:

1. A low profile dilatation catheter comprising an elongate flexible tubular member having proximal and distal extremities and having a flow passage extending therethrough, an inflatable balloon having proximal and distal extremities with the proximal extremity of the balloon connected to the distal extremity of the elongate flexible tubular member so that the interior of the balloon is in fluid communication with the flow passage in the tubular member, a flexible tip secured to the distal extremity of the balloon, a core wire having a tapered distal extremity and extending through the balloon and into the flexible tip, means securing the distal extremity of the core wire to the flexible tip, means for rotating the proximal extremity of the core wire for causing rotation of the flexible tip, a passageway between the core wire and [the inner diameter of the flexible tip] for venting gas from the balloon to ambient without passage of inflation liquid therethrough, and an adapter carried by the proximal extremity of the elongate tubular member which is adapted to supply a liquid to the flow passage for inflating and deflating the inflatable balloon.

2. A catheter as in claim 1 wherein the means for rotating the proximal extremity of the core wire includes means for securing the proximal extremity of the core wire to the proximal extremity of the tubular member so that as the adapter is rotated, the core wire and the tubular member are rotated to provide rotation of the flexible tip.

3. A catheter as in claim 1 wherein said balloon has an inflated diameter of less than approximately two millimeters.

4. A catheter as in claim 3 wherein said flexible tubular member has a diameter of less than approximately 0.020 inch.

5. A catheter as in claim 3 wherein said core wire has a diameter of less than approximately 0.012 inch.

6. A tubular member as in claim 4 wherein said tubular member has a wall thickness of approximately 0.001 inch and an outside diameter of approximately 0.018 inch with an inside diameter of approximately 0.016 inch.

7. A catheter as in claim 1 wherein said passageway is defined by a capillary tube disposed in the distal extremity of the balloon and wherein the core wire extends through the capillary tube.

8. A catheter as in claim 7 wherein the core wire is free to rotate with respect to the distal extremity of the balloon.

9. A catheter as in claim 1 wherein the proximal extremity of the balloon is disposed within the distal extremity of the tubular member.

10. In a balloon dilatation catheter, an elongate flexible tubular member having proximal and distal extremities and having a flow passage extending therethrough, an inflatable balloon carried by the distal extremity of the tubular member and having its interior in communication with the flow passage, the balloon having a distal extremity, a flexible tip secured to the distal extremity of the balloon, a capillary tube disposed in the distal extremity of the balloon, a core wire extending through the flow passage, the balloon and the capillary tube and means securing the core wire to the flexible tip, the core wire and the capillary tube providing an annular flow passage for the venting of air through the interior of the balloon to ambient when the balloon is filled with a liquid.

11. A catheter as in claim 10 together with means secured to the core wire for rotating the core wire for rotating the flexible tip, the core wire being free to rotate with respect to the distal extremity of the balloon.

12. A catheter as in claim 11 wherein the rotating means includes means for limiting the rotation of the core wire.

*13. A low profile fixed-wire dilatation catheter comprising:*

*a) an elongated catheter body having proximal and distal extremities and a fluid flow passageway extending therethrough;*

*b) an inflatable balloon on the distal extremity of the catheter body which has a distal end and which has an interior in fluid communication with the fluid flow passageway in the catheter body;*

*c) a guide member fixed within the catheter which extends through the interior of the balloon and out the distal end thereof and which has a flexible tip mounted on the portion thereof extending out the distal end of the balloon; and*

*d) means disposed between the distal end of the balloon and the portion of the guide member extending therethrough to allow relative rotation therebetween.*

*14. A low profile dilatation catheter comprising:*

*a) an elongated catheter body having proximal and distal extremities and a single lumen extending therethrough;*

*b) an inflatable balloon on the distal extremity of the catheter body having a distal end and an interior in fluid communication with the single lumen in the catheter body;*

*c) a guide member which is disposed within the single lumen of the catheter body, which extends through the interior of the balloon and out the distal end thereof and which has a flexible tip mounted on the portion thereof extending out the distal end of the balloon; and*

*d) means to allow relative rotation between the distal end of the balloon and the guide member.*

* * * * *